US00RE46373E

(19) United States
(12) Reissued Patent
Dyer, Jr. et al.

(10) Patent Number: US RE46,373 E
(45) Date of Reissued Patent: Apr. 25, 2017

(54) OTOLOGIC NANOTECHNOLOGY

(71) Applicant: Hough Ear Institute, Oklahoma City, OK (US)

(72) Inventors: R. Kent Dyer, Jr., Edmond, OK (US); Jack V. D. Hough, Oklahoma City, OK (US)

(73) Assignee: HOUGH EAR INSTITUTE, Oklahoma City, OK (US)

(21) Appl. No.: 14/533,759

(22) Filed: Nov. 5, 2014

Related U.S. Patent Documents

Reissue of:
(64) Patent No.: 8,303,990
Issued: Nov. 6, 2012
Appl. No.: 12/148,738
Filed: Apr. 22, 2008

U.S. Applications:
(63) Continuation of application No. 10/740,110, filed on Dec. 17, 2003, now abandoned.

(60) Provisional application No. 60/434,480, filed on Dec. 18, 2002.

(51) Int. Cl.

| | |
|---|---|
| ***A61K 9/14*** | (2006.01) |
| ***A61K 49/00*** | (2006.01) |
| ***A61K 38/00*** | (2006.01) |
| ***A61K 31/56*** | (2006.01) |
| ***A61K 31/70*** | (2006.01) |
| ***A61K 31/235*** | (2006.01) |
| ***A61K 31/395*** | (2006.01) |
| ***A61F 2/00*** | (2006.01) |
| ***A61K 41/00*** | (2006.01) |
| ***A61K 9/50*** | (2006.01) |
| ***A61N 2/00*** | (2006.01) |
| ***A61K 9/00*** | (2006.01) |
| ***A61K 9/51*** | (2006.01) |
| *A61N 2/06* | (2006.01) |

(52) U.S. Cl.
CPC ..... *A61K 41/00* (2013.01); *A61K 9/0046* (2013.01); *A61K 9/5094* (2013.01); *A61K 9/51* (2013.01); *A61N 2/002* (2013.01); *A61N 2/06* (2013.01)

(58) Field of Classification Search
CPC ..... A61K 9/0046; A61K 9/51; A61K 9/5094; A61K 41/00; A61N 2/002; A61N 2/06
USPC ..... 424/489, 423, 9.1; 514/1.1, 178, 532, 514/563
See application file for complete search history.

(56) References Cited

U.S. PATENT DOCUMENTS

| | | | | |
|---|---|---|---|---|
| 4,501,726 | A | 2/1985 | Schroder et al. | |
| 4,652,257 | A | 3/1987 | Chang | |
| 4,690,130 | A | 9/1987 | Mirell | |
| 5,837,681 | A * | 11/1998 | Magal | 514/8.4 |
| 5,916,539 | A | 6/1999 | Pilgrimm | |
| 5,928,958 | A | 7/1999 | Pilgrimm | A61K 9/5094 424/9.323 |
| 6,014,580 | A | 1/2000 | Blume et al. | |
| 6,121,235 | A * | 9/2000 | Gao | 514/8.4 |
| 6,156,873 | A * | 12/2000 | Krause et al. | 528/395 |
| 6,177,434 | B1 * | 1/2001 | Kopke et al. | 514/46 |
| 6,274,554 | B1 | 8/2001 | Magal et al. | |
| 6,344,357 | B1 | 2/2002 | Rickwood | |
| 6,436,028 | B1 | 8/2002 | Dormer | |
| 6,436,437 | B1 * | 8/2002 | Yatvin et al. | 514/171 |
| 6,479,033 | B1 * | 11/2002 | Reszka | A61K 31/28 424/450 |
| 6,548,264 | B1 | 4/2003 | Tan et al. | |
| 6,767,635 | B1 | 7/2004 | Bahr et al. | |
| 7,189,198 | B2 | 3/2007 | Harburn et al. | |
| 2001/0007897 | A1 * | 7/2001 | Agarwal et al. | 528/15 |
| 2002/0086842 | A1 | 7/2002 | Plank et al. | |
| 2003/0215394 | A1 | 11/2003 | Short et al. | |
| 2003/0229333 | A1 * | 12/2003 | Ashton et al. | 604/514 |
| 2010/0009872 | A1 * | 1/2010 | Eid et al. | 506/26 |
| 2010/0029016 | A1 * | 2/2010 | Dickson et al. | 436/528 |

FOREIGN PATENT DOCUMENTS

| | | | |
|---|---|---|---|
| DE | 43 09 333 | A1 | 9/1994 |
| WO | WO 98/01160 | | 1/1998 |
| WO | WO 99/60998 | | 12/1999 |
| WO | WO 02/056890 | A1 | 7/2002 |
| WO | WO 03/059194 | A2 | 7/2003 |
| WO | WO 2004/006765 | A1 | 1/2004 |

OTHER PUBLICATIONS

GW Hicks. Intratympanic and round-window drug therapy: Effect on cochlear tinnitus. International Tinnitus Journal, 4(3):144-147 (1998).*

Goycoolea MV and Lundman L. Round window membrane. Structure function and permeability: A review. Microsopy Research and Technique, 36:201-211 (1997).*

Ghosh PK. Hydrophilic polymeric nanoparticles as drug carriers. Indian Journal of Biochemistry & Biophysics. vol. 37, Oct. 2000, pp. 273-282.*

Lackey et al.; A Biomimetic pH-Responsive Polymer Directs Endosomal Release and Intracellular Delivery of an Endocytosed Antibody Complex; Bioconjugate Chem. 2002, 13, 996-1001.

(Continued)

*Primary Examiner* — Shri Ponnaluri
(74) *Attorney, Agent, or Firm* — Gilberto M. Villacorta; Nicholas M. Lagerwall; Foley & Lardner LLP

(57) ABSTRACT

Diagnosing or treating a human ear includes transporting a conjugated nanoparticle or a magnetically responsive nanoparticle into a human's middle or inner ear. Otologic nanophoresis includes electrically, magnetically or electromagnetically driving a nanoparticle through a membrane of the ear, including a tympanic membrane, a round window membrane, an oval window membrane, or a circulatory membrane. An otologic diagnostic device includes a nanoparticle conjugated with a material selected from the group consisting of lipids, proteins, growth factors, growth hormones, antioxidants, free radical scavengers, steroid preparations, and metabolically active substances; an otologic therapeutic device includes the same categories of substances and chemotherapeutic drugs. Another otologic composition includes a nanoparticle conjugated with a substance perceptible to magnetic resonance imaging.

32 Claims, 6 Drawing Sheets

(56) References Cited

OTHER PUBLICATIONS

Wilhelm et al.; Intracellular uptake of anionic superparamagnetic nanoparticles as a function of their surface coating; Biomaterials 24 (2003) 1001-1011.
Jung Hae Suh et al.; Efficient active transport of gene nanocarriers to the cell nucleus; PNAS vol. 100 No. 7 Apr. 1, 2003, pp. 3878-3882.
Wolfgang Schuti et al.; Biocompatible Magnetic Polymer Carriers for In Vivo Radionuclide Delivery; Artif Organs, vol. 23, No. 1, 1999, 98-103.
Nicoli et al.; Design of triptorelin loaded nanospheres for transdermal iontophoretic administration; International Journal of Pharmaceutics 214 (2001) 31-55.
Brigger et al.; Nanoparticles in cancer therapy and diagnosis; Advanced Drug Delivery Reviews 54 (2002) 631-651.
Duclairoir et al.; -Tocopherol encapsulation and in vitro release from wheat gliadin nanoparticles; J. Microencapsulation, 2002, vol. 19, No. 1, 53-60.
Chang. "Adriamycin-loaded immunological magnetic nanoparticles: Site-specific targeting of the nanoparticles in rabbits guided by an outside magnetic field." *Chinese Journal of Biomedical Engineering* 15 (1996): 354-359.
"Magnets Help Target Gene Therapy", Press release, 2002, Bioelectromagnetics Society.
Buske et al.; Magnetic Sizing of Magnetic Nanoparticles; Mediport Kardiotechnik GmBH, 2000; 2 pages.
Tartaj et al.; The preparation of magnetic nanoparticles for applications in biomedicine; J. Phys. D: Appl. Phys. 36 (2003) R182-R197.
Berry et al.; Functionalisation of magnetic nanoparticles for applications in biomedicine; J. Phys. D: Appl . Phys. 36 (2003) R198-R206.
Barbic; Single Domain Magnets in Bio-Medical Applications; European Cells and Materials vol. Suppl. 2, 2002 (pp. 132-134).
Mornet et al.; Maghemite@silica Nanoparticles for Biological Applications; vol. Suppl. 2, 2002 (pp. 110-113).
Kostergaard et al.; Magnetic Vectoring of Magnetically Responsive Nanoparticles (MNP) within the Murine Peritoneum; Journal of Magnetism and Magnetic Materials; vol. 311, Issue 1, Apr. 1, 2007, pp. 330-335.
Correa-Duarte et al.; Control of Packing Order of Self-Assembled Monolayers of Magnetite Nanoparticles with and without Si02 coating by Microwave Irradiation; Lanmuir 1998, 14, 6430-6435.
Farokhzad et al; Nanoparticle-Aptamer Bioconjugates; Cancer Research 64, 7668-7672, Nov. 1, 2004.
Goya et al; Static and dynamic magnetic properties of spherical magnetite nanoparticles; Journal of Applied Physics vol. 94, No. 5, Sep. 1, 2003, pp. 3520-3528.
Shirwani et al. (Effect of transtympanic injection on cochlear blood flow, auditory sensitivity in the guinea pig, in Am J Otol Mar. 1998; 19(2) Abstract for pp. 230-235).*
Young Zhang et al.; Surface Modification of superparamagnetic magnetite nanoparticles and their intracellular uptake; Biomaterials 23 (2002) 1553-1561.
Jayanth Panyam et al.; Rapid endo-lysosomal escape poly(DL-lactide-co-glycolide) nanoparticles: implications for drug and gene delivery; The FASEB Journal vol. 16 Aug. 2002 pp. 1217-1226.
Swayam Prabha et al.; Size-dependency of nanoparticle-mediated gene transfection: studies with fractionated nanoparticles; International Journal of Pharmaceutics 244 (2002) 105-115.
Chantal A. Lackey et al.; A Biomimetic pH-Responsive Polymer Directs Endosomal Release and Intracellular Delivery of an Endocytosed Antibody Complex; Bioconjugate Chem. 2002, 13, 996-1001.
C. Wilhelm et al.; Intracellular uptake of anionic superparamagnetic nanoparticles as a function of their surface coating; Biomaterials 24 (2003) 1001-1011.
Jayanth Panyam et al.; Biodegradable nanoparticles for drug and gene delivery to cells and tissue; Advanced Drug Delivery Reviews 55 (2003) 329-347.
Murthy et al.; Bioinspired pH-Responsive Polymers for the Intracellular Delivery of Biomolecular Drugs; Bioconjugate Chem. 2003, 14, 412-419.
Junghae Suh et al.; Efficient active transport of gene nanocarriers to the cell nucleus; PNAS vol. 100 No. 7 Apr. 1, 2003, pp. 3878-3882.
Liu et al; Nanoparticles of Compacted DNA Transfect Postmitotic Cells; The Journal of Biological Chemistry, vol. 278, No. 35, Issue of Aug. 29, pp. 32578-32586 2003.
X.X. He et al. A Novel Method for Efficient Gene Delivery Using Amino-Modified Silica coated Magnetic Nanoparticles; Rev. Adv. Mater. Sci. 5 (2003) 375-380.
Fadee Mondalek; Concerns Regarding the Permeability of the Round Window Membrane (RWM) to Magnetite Nanoparticles Attached to a Drug/Gene; Oct. 28, 2003; OU Health Sciences Center; pp. 1-3.
Rachel A. Jones et al.; Poly(2-alkylacrylic acid) polymers deliver molecules to the cytosol by pH-sensitive disruption of endosomal vesicles; Biochem. J. (2003) 372, 65-75.
Nanoparticle News; MRI Transformed into Cancer Treatment Tool; Oct. 2002; 18 pages.
Plank et al.; The Magnetofection Method: Using Magnetic Force to Enhance Gene Delivery; Biol. Chem., vol. 384, pp. 737-747, May 2003.
S. Utreja et al.; Lipoprotein-mimicking biovectorized systems for methotrexate delivery; Pharm Acta Helv. Jun. 1999; 73 (6):275-9.
Wolfgang Schutt et al.; Biocompatible Magnetic Polymer Carriers for In Vivo Radionuclide Delivery; Artif Organs, vol. 23, No. 1, 1999, 98-103.
S. Nicoli et al.; Design of triptorelin loaded nanospheres for transdermal iontophoretic administration; International Journal of Pharmaceutics 214 (2001) 31-55.
Irene Brigger et al.; Nanoparticles in cancer therapy and diagnosis; Advanced Drug Delivery Reviews 54 (2002) 631-651.
C. Duclairoir et al.; -Tocopherol encapsulation and in vitro release from wheat gliadin nanoparticles; J. Microencapsulation, 2002, vol. 19, No. 1, 53-60.
Bruce M. Moskowitz; Domain Theory; Jun. 1991; 12 pages.
Dow Corning Corporation; The Basics of Silane Chemistry; 2005; 25 pages.
N. Buske et al.; Magnetic Sizing of Magnetic Nanoparticles; Mediport Kardiotechnik GmBH, 2000; 2 pages.
Pankhurst et al; Applications of magnetic nanoparticles in biomedicine; J. Phys. D: Appl. Phys. 36 (2003) R167-R181.
Pedro Tartaj et al.; The preparation of magnetic nanoparticles for applications in biomedicine; J. Phys. D: Appl. Phys. 36 (2003) R182-R197.
Catherine C. Berry et al.; Functionalisation of magnetic nanoparticles for applications in biomedicine; J. Phys. D: Appl. Phys. 36 (2003) R198-R206.
Joseph F. Bringley et al.; Controlled Chemical and Drug Delivery via the Internal and External Surfaces of Layered Compounds; Journal of Dispersion Science and Technology; vol. 24, Nos. 3 & 4, pp. 589-605, 2003.
Mladen Barbic; Single Domain Magnets in Bio-Medical Applications; European Cells and Materials vol. Suppl. 2, 2002 (pp. 132-134).
S. Mornet et al.; Maghemite@silica Nanoparticles for Biological Applications; vol. Suppl. 2, 2002 (pp. 110-113).
Jim Kostergaard et al.; Magnetic Vectoring of Magnetically Responsive Nanoparticles (MNP) within the Murine Peritoneum; Journal of Magnetism and Magnetic Materials; vol. 311, Issue 1, Apr. 2007, pp. 330-335.
Miguel A Correa-Duarte et al.; Control of Packing Order of Self-Assembled Monolayers of Magnetite Nanoparticles with and without SiO2 coating by Microwave Irradiation; Lanmuir 1998, 14, 6430-6435.
Medical News Today; Targeted drug delivery achieved with nanoparticle-aptamer bioconjugates; Nov. 6, 2005; 3 pages.
Omid C. Farokhzad et al.; Nanoparticle-Aptamer Bioconjugates; Cancer Research 64, 7668-7672, Nov. 1, 2004.

(56) References Cited

OTHER PUBLICATIONS

Thornton AS et al; Magnetic Assisted Navigation in Electrophysiology and Cardiac Resynchronisation: A Review; Indian Pacing and Electrophysiology Journal , 6(4): 202-213 (2006).
G.F. Goya et al; Static and dynamic magnetic properties of spherical magnetite nanoparticles; Journal of Applied Physics vol. 94, No. 5, Sep. 1, 2003, pp. 3520-3528.

* cited by examiner

OTOLOGIC NANOTECHNOLOGY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application *is a reissue of U.S. Pat. No. 8,303,990 (previously U.S. patent application Ser. No. 12/148,738, filed Apr. 22, 2008), which is a continuation of U.S. patent application Ser. No. 10/740,110, filed Dec. 17, 2003 (now abandoned), which* claims the benefit of U.S. Provisional Application No. 60/434,480 entitled OTOLOGIC NANOTECHNOLOGY filed [on ] Dec. 18, 2002[, and claims the benefit of and is a continuation of U.S. Ser. No. 10/740,110, filed Dec. 17, 2003 now abandoned].

BACKGROUND OF THE INVENTION

This invention relates generally to applications of nanotechnology to the human ear. These applications of otologic nanotechnology can be for diagnostic, therapeutic or other purposes.

Nanotechnology involves the application of molecular particles, referred to as nanoparticles, such as ones approximately the size of 10 hydrogen atoms. In general, nanoparticles typically have at least one dimension measured in nanometers (for example, from about one to 100 nanometers). Otologic nanotechnology involves the use of nanoparticles in applications pertaining specifically to the human ear.

Diagnosing and treating problems in the human ear can be difficult. The middle ear and the inner ear are small, in the middle of the head and surrounded by bone. These characteristics make it difficult to access the middle and inner ears such as when needed to address issues of hearing loss, ear infections and growths such as tumors (malignant and non-malignant), and structural problems such as ossicular damage, for example. The outer ear, separated from the middle ear by the tympanic membrane, is more readily accessible.

In view of the foregoing, there is the need for improved techniques for accessing, diagnosing and treating the human ear.

SUMMARY OF THE INVENTION

The present invention meets the aforementioned need by providing novel and improved applications of nanotechnology in the field of otology, which applications provide techniques for accessing, diagnosing and treating the human ear.

The present invention more particularly provides the following. A method of diagnosing or treating a human ear includes transporting a conjugated nanoparticle or a magnetically responsive nanoparticle into a middle or inner ear of a human. Otologic nanophoresis comprises electrically, magnetically or electromagnetically driving a nanoparticle through a membrane of a human ear, including a tympanic membrane, a round window membrane, an oval window membrane, or a circulatory membrane. An otologic diagnostic device includes a nanoparticle conjugated with a material selected from the group consisting of lipids, proteins, growth factors, growth hormones, antioxidants, free radical scavengers, steroid preparations, and metabolically active substances; an otologic therapeutic device includes the same categories of substances as well as chemotherapeutic drugs. Another otologic composition includes a nanoparticle conjugated with a substance perceptible to magnetic resonance imaging.

Therefore, from the foregoing, it is a general object of the present invention to provide novel and improved applications of nanotechnology in the field of otology useful for accessing, diagnosing and treating the human ear. Other and further objects, features and advantages of the present invention will be readily apparent to those skilled in the art when the following description of the preferred embodiments is read in conjunction with the accompanying drawings.

DETAILED DESCRIPTION OF THE INVENTION

Figure 1:
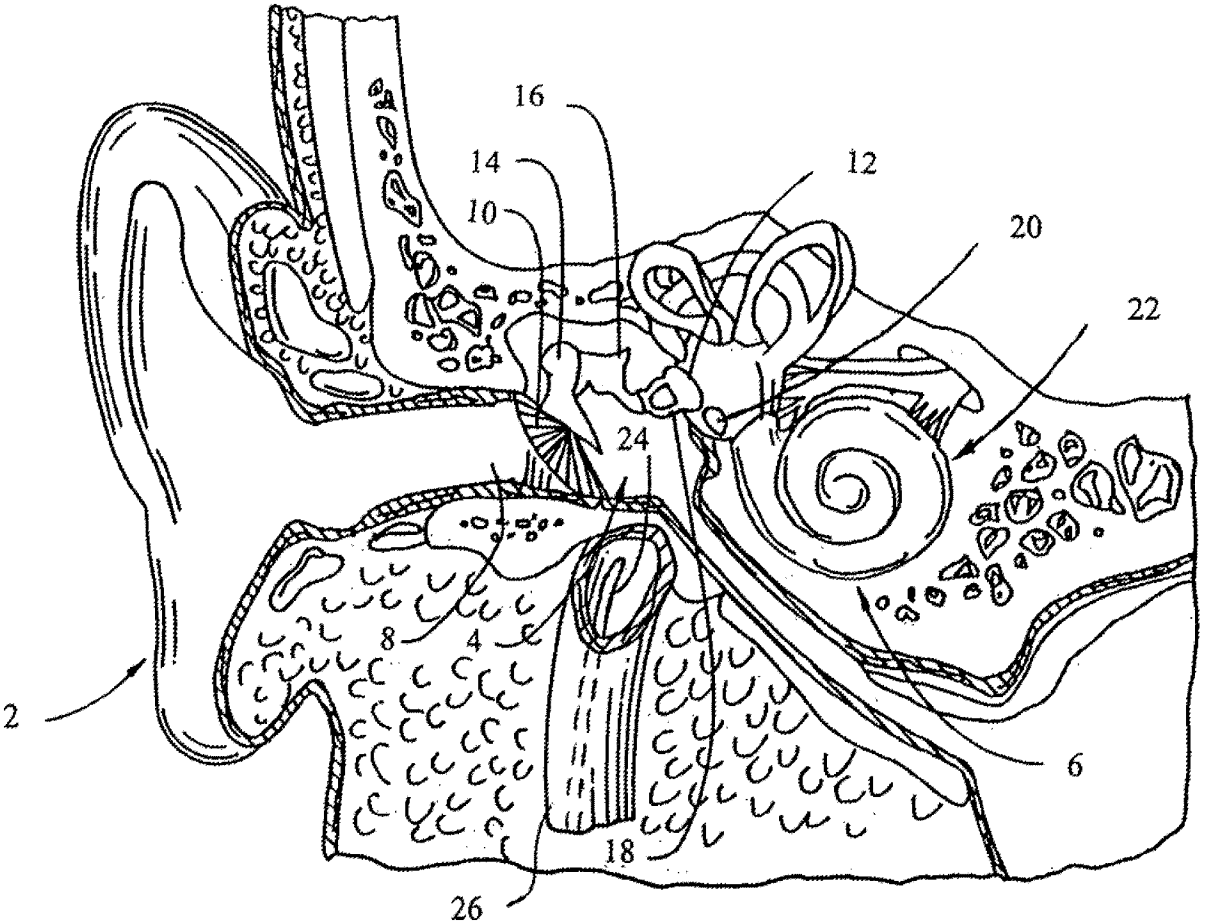
FIG. 1 is a schematic drawing of a human ear having a catheter in a jugular vein for delivering nanoparticles to inner ear circulation.

Examples of nanoparticles relevant to the present invention include:

1) Water soluble polymers
2) Uncharged hydrophilic polymers (e.g., polyethyleneglycol, or PEG)
3) Micelles composed of copolymers with hydrophilic shells and amino acid cores
4) Dendrimers (branched macro molecules less than five nanometers in diameter which have drug carrying capacity; these have been used in cancer therapy for delivery of Cisplatin and Methotrexate)
5) Magnetic targeted carriers (MTCs) (nanoparticles composed of metallic iron and activated carbon prepared by a high energy milling process).

Broader aspects of the present invention are not limited to the foregoing.

Conjugated nanoparticles are nanoparticles combined with another substance. For example, MTCs have an activated carbon shell which can serve as a carrier or vehicle for delivery of specific pharmaceutical agents. For example, steroids (e.g., dexamethasone or methyl prednisolone) can be attached to the activated carbon molecule for delivery into the inner ear in response to an externally applied magnetic field. Other pharmaceutical agents to conjugate with nanoparticles for otologic nanotechnology include, but are not limited to, those described throughout this specification. Conjugation of these substances to nanoparticles is accomplished in suitable manner known in the art to establish suitable coupling, such as chemical bonding, of the materials.

Delivery of conjugated nanoparticles to the ear may occur via the circulatory system, across the tympanic membrane, through the eustachian tube, or with direct middle ear application via tympanotomy exposure. Following are examples, some of which refer to the drawings in which a human ear is represented. The schematically illustrated ear includes an outer ear 2, a middle ear 4, and an inner ear 6. The outer ear 2 has an outer ear canal 8 which is normally closed at its inner end by tympanic membrane, or eardrum, 10. Also pertinent is an ossicular chain, which if intact extends from tympanic membrane 10 to oval window 12 defining an entrance to the inner ear 6. The intact ossicular chain extends through the middle ear 4 and includes a malleus 14, an incus 16, and a stapes 18. A properly functioning ossicular chain transmits vibrations from the tympanic membrane 10 in series through the malleus 14, the incus 16 and the stapes 18 to the oval window 12. Vibrations at the oval window 12 stimulate the inner ear 6 whereby the person perceives the sound received in the outer ear 2. Also marked in the drawings are round window membrane 20 and cochlea 22.

Figure 2:
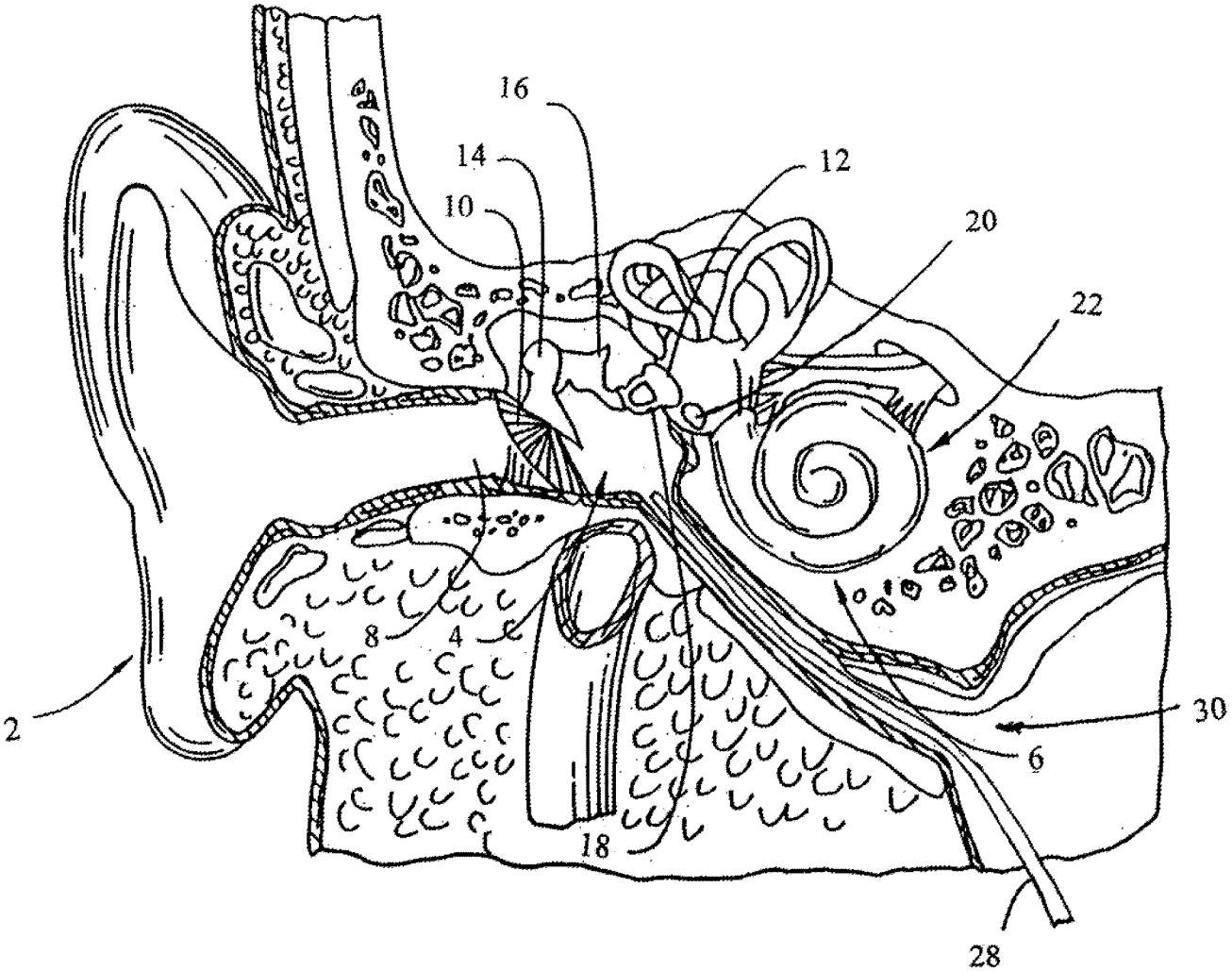
FIG. 2 is a schematic drawing of a human ear having a Eustachian tube catheter passed into the middle ear via the nasopharynx for delivering nanoparticles.

Delivery of nanoparticles via the circulation is guided by an external magnetic field if MTCs or other magnetic nanoparticles are used as a carrier. For example, a catheter is placed into the circulatory system near the inner ear target and magnetically active particles are carried through the catheter and into the inner ear in response to an externally placed magnetic or electromagnetic field. Referring to FIG. 1, such nanoparticles are illustrated to be delivered via a catheter 24 inserted in a jugular vein 26. Catheterization through the Eustachian tube is another delivery technique. For example, FIG. 2 illustrates a catheter 28 passed through the nasopharynx and into Eustachian tube 30. Such catheters and their manipulation/use are as known in the art. See FIG. 4 for a representation of an externally applied magnetic field.

Figure 3:
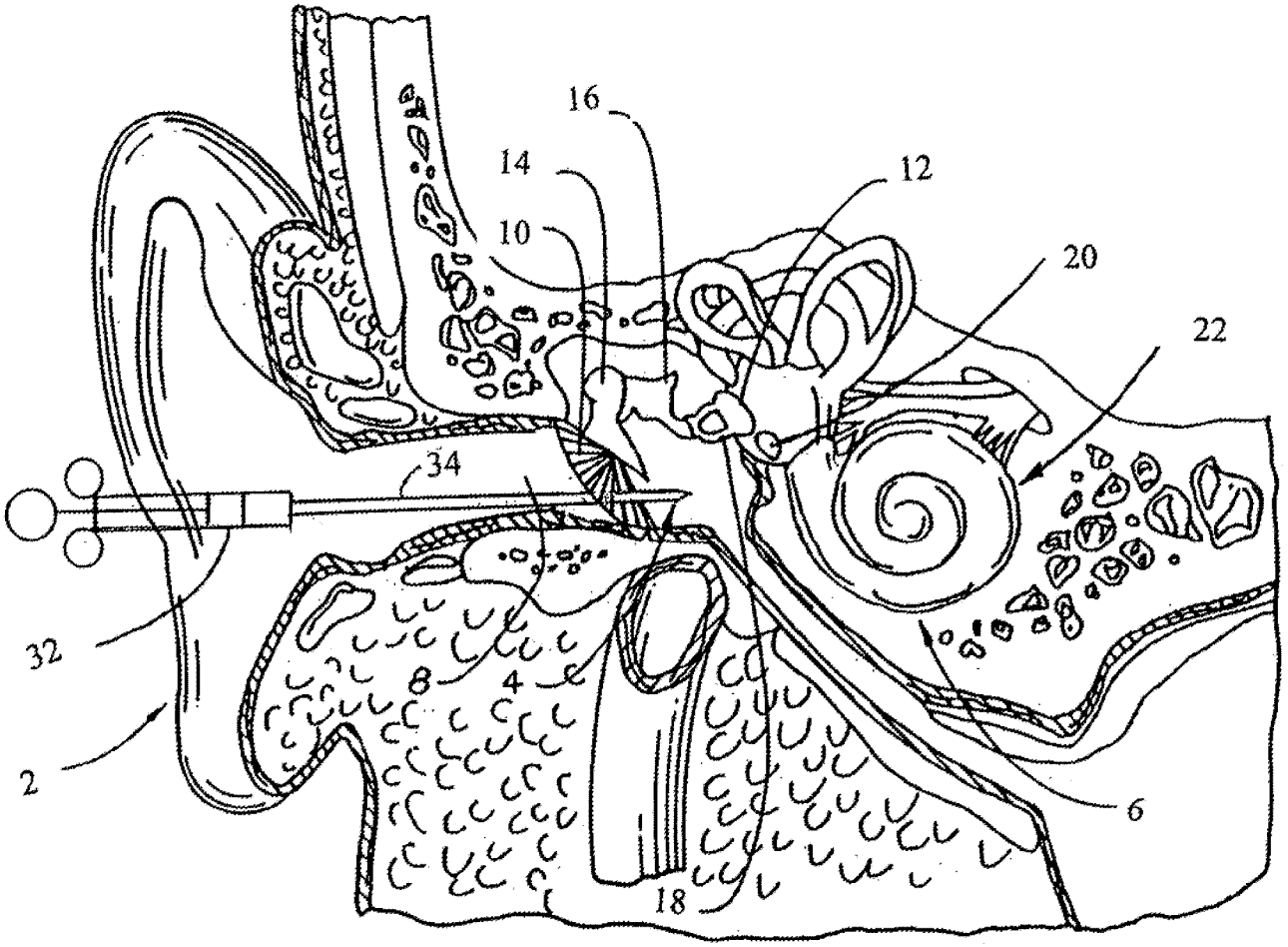
FIG. 3 is a schematic drawing of a human ear in which a syringe needle is inserted through the tympanic member for intratympanic delivery of nanoparticles.
Figure 4:
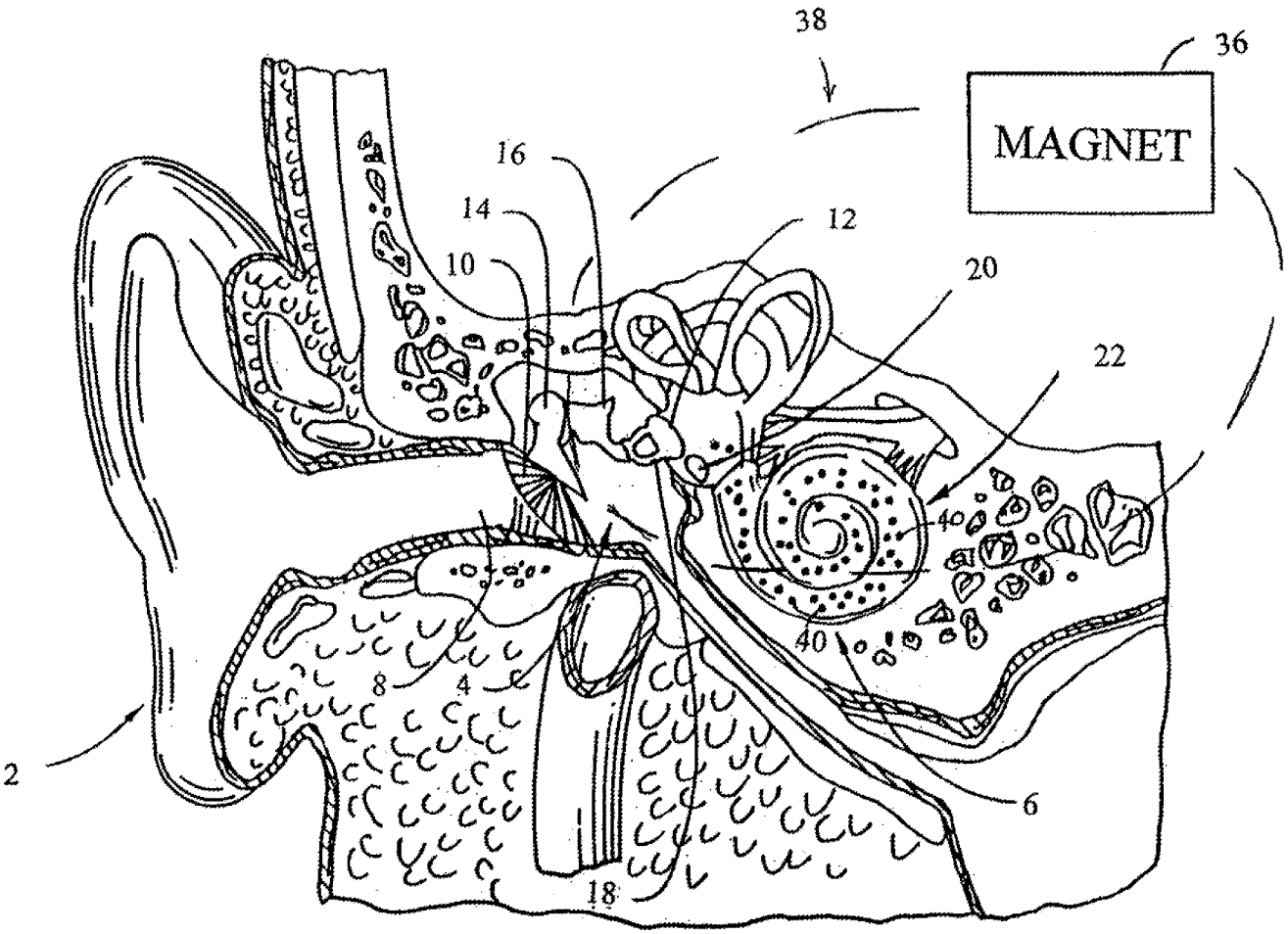
FIG. 4 is a schematic drawing of a human ear having nanoparticles distributed throughout the cochlea in response to a magnetic field from an external magnet.

Middle ear delivery of conjugated magnetically/electromagnetically responsive nanoparticles is facilitated by, for example, a transtympanic injection of MTCs into the middle ear (such as via the tympanic membrane using a tympanotomy approach). FIG. 3 schematically illustrates a one cubic centimeter tuberculin syringe 32 attached to a 27-gauge spinal needle 34 inserted into the tympanic membrane for intratympanic delivery of nanoparticles. Delivery from the middle ear to the inner ear, across the round window membrane, is promoted by an externally placed magnetic field in the ear canal which drives the MTCs across the round window membrane into the inner ear fluids (see FIG. 4 representing an external magnet 36 providing a magnetic field 38 that attracts magnetically responsive nanoparticles 40 for distribution throughout the cochlea 22; the magnet 36 can be implemented magnetically or electromagnetically, and another example is to implement the driving force by an electrical differential, any of which is located relative to the patient's ear or head as appropriate to obtain the desired direction(s) of nanoparticle movement). Thus, the present invention provides otologic nanophoresis whereby a (i.e., one or more)) nanoparticle is driven through a membrane of a human ear. The membrane can include a tympanic membrane of the human ear, a round window membrane of the human ear, an oval window membrane of the human ear, or a circulatory membrane in the human ear. The driving occurs electrically, electromagnetically, or magnetically.

Figure 5:
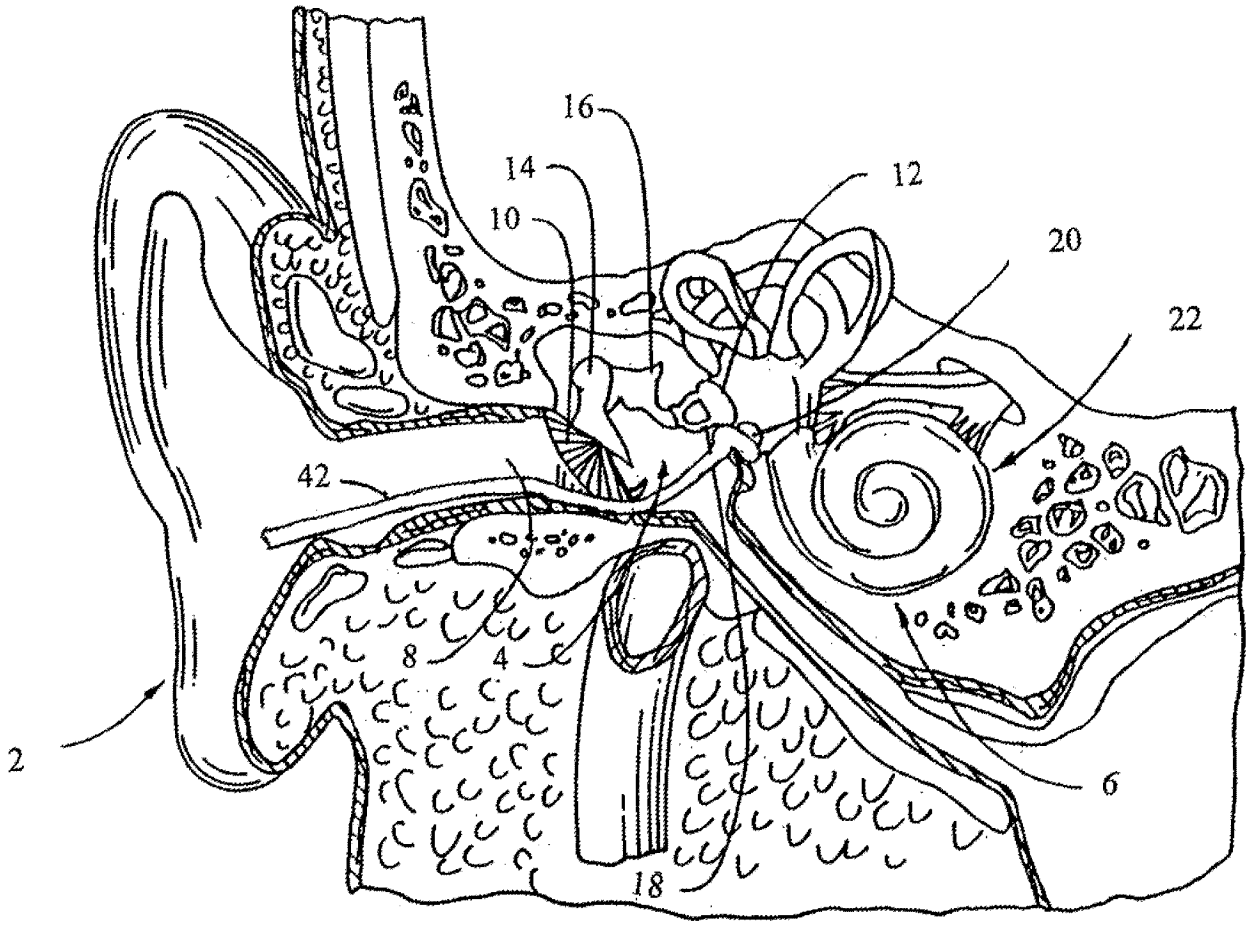
FIG. 5 is a schematic drawing of a human ear having a catheter placed through the tympanic membrane into the middle ear adjacent the round window membrane for delivering nanoparticles to the inner ear.

Another method of otologic delivery of nanoparticles, which need not be magnetic, involves the use of a microcatheter, such as the intra EAR round window catheter (RW Mc-Cath™). Referring to FIG. 5, such a catheter 42 is introduced (such as via a tympanotomy directly or endoscopically) into the middle ear from the ear canal and the distal tip of the catheter 42 is placed immediately adjacent to the round window membrane 20. Fluid containing nanoparticles is then passed into the catheter 42 and this material is brought into intimate association with the round window membrane facilitating diffusion of nanoparticle carriers into the inner ear. These micro-catheters allow continual controlled pharmaceutical delivery to the round window membrane of the middle ear and can remain in place for up to twenty-nine days (according to one micro-catheter use protocol).

Transport of nanoparticles across membranes such as the round window membrane may be facilitated by several mechanisms. For example: lipophilic polymers which pass easily across membranes are conjugated with the nanoparticles; combination with hyaluronidase increases membrane permeability; conjugation with magnetic carriers which respond to externally directed magnetic fields, thereby driving nanoparticles across the membrane by magnetic/electromagnetic attraction or repulsion.

Specific conjugated nanoparticles to be delivered by any suitable one or more of the foregoing techniques have coupled chemical or biological substances (the word "or" including both) that are to be used in the ear regions to which they are delivered. Following are examples.

Nanoparticles coupled with chemical or biological substances, when introduced into an ear, can be used to label middle ear substances for diagnostic investigation.

Occasionally patients who have skull base fractures related to head trauma will develop leakage of cerebrospinal fluid (CSF) into the middle ear, which ultimately drains out of the ear canal or out the eustachian tube into the nose. A way of definitively diagnosing CSF in the middle ear would be very helpful. A serologic assay for CSF has been developed, which assay is specific for beta 2 transferrin. Beta 2 transferrin is present in spinal fluid and is not found in other fluids within the body. An otologic nanoparticle which specifically binds to beta 2 transferrin is used to detect this. That is, uptake of this marker in the middle ear suggests the presence of spinal fluid.

Another example of labeling includes binding to nanoparticles biologically active materials that are preferentially absorbed by diseased middle ear tissues (e.g., for early diagnosis of neoplasm, cholesteatoma, or other pathological processes before they can be detected by conventional scanning techniques presently available). For example, bio-integration is used for labeling specific cellular elements that are unique to that particular disease process. The process of bio-integration involves incorporation of nanoparticles within the cell membrane of tissues under investigation or uptake into the cell cytoplasm. Certain protein and lipid nanoparticles may be then taken into the cell nucleus to become incorporated into the DNA structure of the cell. For example, tumor cells with rapid mitotic activity may specifically bind nanoparticles which have been conjugated to proteins needed for cellular differentiation and division. A nanoparticle which is selectively absorbed by tumor cells, and which is conjugated with the contrast medium gadolinium perceptible to magnetic resonance imaging (MRI), increases the sensitivity of MRI for detecting a neoplastic process within the temporal bone. Two methods of such labeling are the following. The first involves binding of gadolinium to an activated carbon molecule on the nanoparticle carrier. A second method of labeling involves using an antibody (a protein) which binds gadolinium to a nanoparticle. Thus, the present invention also provides an otologic composition comprising a nanoparticle conjugated with protein that binds with pathological tissue in a human ear. This can further comprise a therapeutic substance conjugated with the nanoparticle for treating pathological tissue to which the protein binds.

Other therapeutic applications of nanoparticles in the middle ear and inner ear include the following examples.

Nanoparticles can be conjugated with chemotherapeutic drugs or metabolically active substances which selectively bind to pathological tissues to promote healing, retard tumor growth (malignant or non-malignant), or resolve chronic inflammation or infection in the middle ear (including a combination of the foregoing).

An otologic growth composition comprises a nanoparticle conjugated with a growth factor or a growth hormone. As an example, nanoparticles bound to growth factors are applied to tympanic membrane perforations to promote healing of the perforation. Growth factors which promote angiogenesis can be delivered either topically or via the circulation. The binding of these factors to the target is facilitated by nanoparticles which are designed to adhere to breaks in the epithelial surface of the tympanic membrane. Nanoparticles which bind to fibrin exudate, for example, tend to preferentially attach to surfaces which are in the process of healing, such as a tympanic membrane perforation. As another example, magnetically charged nanoparticles conjugated with growth factors are concentrated in the region of the tympanic membrane or middle ear or inner ear by an externally applied magnetic field which is introduced into the ear canal.

Nanoparticles bound to growth factors are applied directly to the ossicular chain to promote osteogenesis in patients with specific ossicular pathology (e.g., incus necrosis). Growth factors attached to the ossicular chain stimulate ingrowth of new blood vessels as well as osteocytes. This process involves stimulation of fibrous tissue as well as the possibility of new bone formation to promote healing of fractures of the ossicular chain. Growth factors also stimulate ingrowth of mucosa around a homograft, autograft or ossicle replacement prosthesis in order to promote bio-integration of the prosthesis into the middle ear and reduce the possibility of foreign body reaction. For example, homograft femur for creating ossicular replacement prostheses has been used for many years. These homograft ossicles, when placed into the middle ear of individuals with conductive or mixed hearing loss to reconstruct the ossicular chain, frequently become bio-integrated. New osteocytes are often seen and these homografts are usually covered by living mucosa when they are examined at a later date. In accordance with the present invention, nanoparticles are used to provide factors necessary for enhancing mucosalization and in-growth of new osteocytes into homograft ossicles, thereby facilitating bio-integration.

Chemotherapeutic agents (e.g., Methotrexate) are concentrated within the tumor by binding to dendrimers or other lipophilic polymers which leak out of permeable vascular channels within tumor tissues, preferentially concentrating the drug within the tumor itself and thereby retarding tumor growth.

Conjugated nanoparticles bound to antibiotics are directed against inflammatory tissues in the middle ear and mastoid by combining these antibiotics with lipophilic polymers which are able to penetrate cell wall membranes. Concentration of antibiotics inside the middle ear and mastoid cavity are enhanced by using magnetically targeted carriers with an attached antibiotic that are directed to the ear by an externally placed magnetic or electromagnetic field. A third mechanism to enhance delivery of drugs to areas of infection within the ear uses the process of phagocytosis of polymers by inflammatory cells such as macrophages. In the process of phagocytosis, the macrophage literally engulfs the lipophilic carrier with attached antibiotic enhancing delivery of the antibiotic inside the macrophage where killing of bacteria normally occurs.

Nanoparticles bound to steroid preparations or other metabolically active agents are diffused across the round or oval window membranes (including across both) into the inner ear. Another way to deliver them is via the circulation. These are used for treatment of various conditions that alter inner ear physiologic function, such as Meniere's disease or autoimmune inner ear disturbances, for example. The oval window membrane is permeable to various metabolically active substances such as lipophilic polymers, dendrimers, uncharged hydrophilic polymers, and MTCs which all act to increase membrane permeability. This increases diffusion of pharmaceutical agents across the membrane barrier.

A major problem encountered with transtympanic administration of drugs to the inner ear relates to inconsistent absorption of the substances across the round window membrane. Nanoparticle carriers, by improving round window membrane transport, provide delivery of drugs intended to be in a more consistent and reliable fashion than is presently possible into the inner ear. The issue of round window membrane transport is particularly applicable in the treatment of Meniere's disease. Gentamycin, which is a selectively ototoxic antibiotic acting primarily on the vestibular system, can be administered transtympanically for delivery to the inner ear in patients with Meniere's disease. However, the absorption of Gentamycin across the round window membrane is extremely variable between patients. Therefore, it is difficult to establish the optimal dose of Gentamycin delivery in treatment of Meniere's. Preferably a nanoparticle carrier for Gentamycin provides delivery of the drug to the inner ear.

Damage to cochlear and vestibular neuro-elements related to external assaults such as viral or bacterial infection, ototoxic drugs (e.g., Cisplatin/arninoglycoside antibiotics) and acoustic trauma may be either prevented or repaired via the introduction of conjugated nanoparticles into the inner ear. Conjugated nanoparticles deliver substances which either promote hair cell regeneration or make neuro-elements within the labyrinth resistant to toxins or acoustic trauma. Certain chemicals, such as free radical scavengers and antioxidants, have been found in animal models to protect the inner ear from sensorineural hearing loss if applied prior to noise exposure. These agents may also be able to reverse cochlear hair cell injury if delivered soon after noise exposure has occurred. Thus, the present invention provides a protective composition for cochlear and vestibular neuroelements, comprising a nanoparticle conjugated with at least one of an antioxidant and a free radical scavenger.

More particularly, repair or prevention of hair cell damage in the inner ear secondary to noise exposure is ultimately related to reduction of free radicals or reactive oxygen species (ROS). Noise exposure has been shown to increase intracochlear free radical formation. The inner ear combats free radical damage by activation of antioxidant enzymes. Antioxidants such as salicylate plus N-L acetylcysteine (L-NAC), iron chelators and reduced glutathione (GSH) have been shown to prevent noise induced hair cell loss in chinchillas. Assuming these protect noise induced hearing loss in humans, combining these compounds with nanoparticles which enhance round window membrane permeability is intended to protect individuals who are exposed to loud noises (such as soldiers) from experiencing hair cell damage and irreversible hearing loss.

Figure 6:
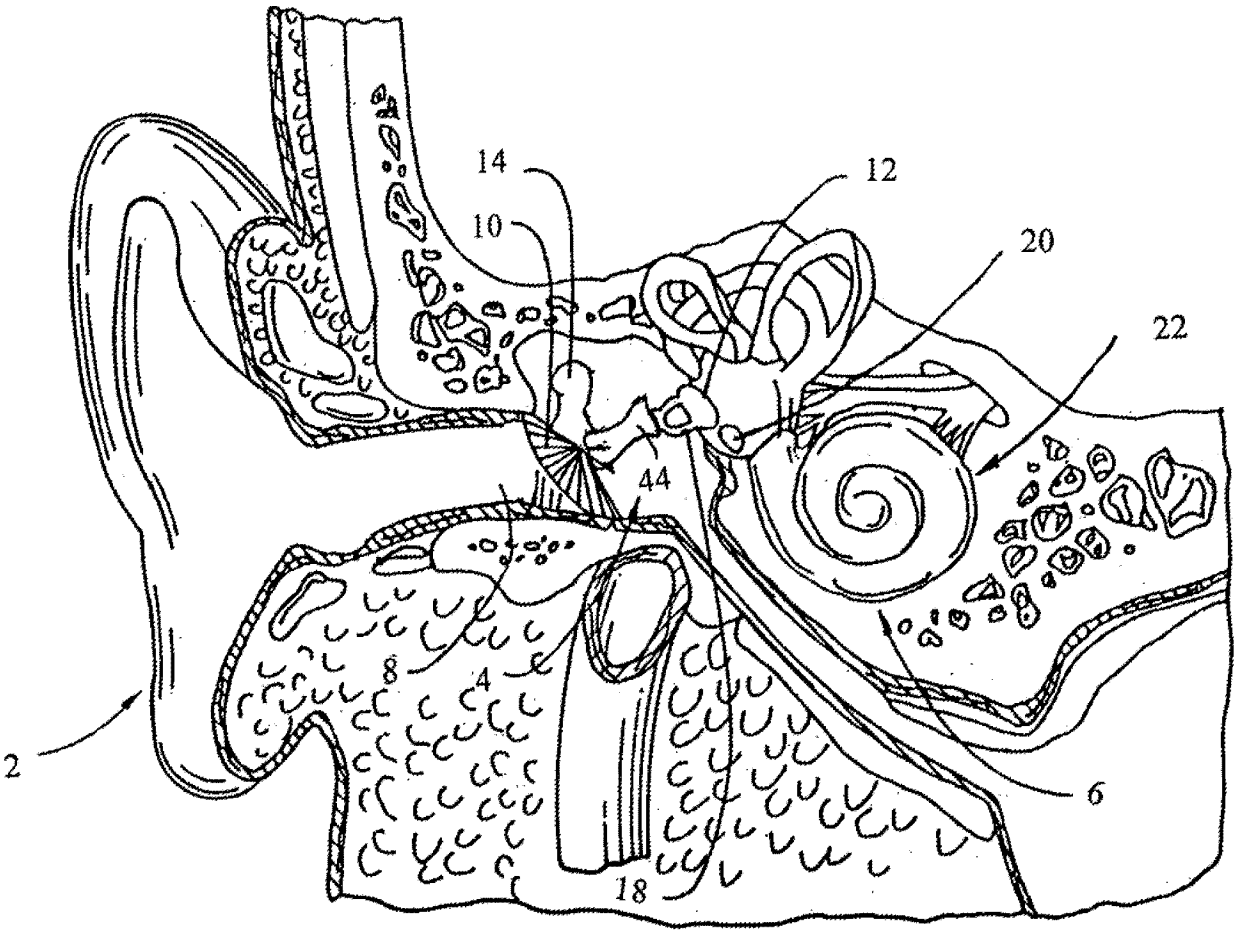
FIG. 6 is a schematic drawing of a human ear in which a homograft femur ossicular transplant has been implanted between the stapes and malleus and coated with magnetically responsive nanoparticles.

Another therapeutic application of nanoparticles involves transmission of vibrational energy into the inner ear across the ossicular chain or directly across the round window or oval window membrane itself. U.S. Pat. No. 6,436,028, which is incorporated herein by reference, discloses the concept of a biomagnetic drive system in which magnetically responsive material is attached to a moveable body for transmission of vibrational energy into the inner ear in response to an electromagnetic field. The magnetically responsive material can be physiologically attached to its target tissue within the ear. In the present invention, homograft or autograft tissues are coated with magnetically active nanoparticles, thereby making the ossicular chain with which they are grafted magnetically responsive. For example, particular target tissues within the middle ear are homograft femur ossicular transplants fashioned by a microlathing process using homograft femur cortex which is sculpted into various prosthesis designs. Three basic ossicular replacement prosthesis designs have been created at the Otologic Medical Clinic, Oklahoma City, Okla., including a stapes prosthesis (S), an incus replacement prosthesis (SHM), and an incus-stapes replacement prosthesis (FPM). FIG. 6 schematically illustrates a homograft femur ossicular transplant 44 that has been coated with magnetically responsive nanoparticles and inserted between the stapes and malleus in a patient with incus necrosis. Another application of magnetically active nanoparticles is the coating of a middle ear prosthesis with them, which when implanted into the middle ear makes the ossicular chain magnetically active; this prosthesis may be composed of synthetic materials such as hydroxyapatite, titanium, gold, or polyethylene. The foregoing middle ear vibratory examples allow the ossicular chain to vibrate in response to an externally applied magnetic or electromagnetic field, providing improved hearing for individuals with mixed, conductive, and sensorineural hearing loss.

From the foregoing, the present invention also provides an otologic diagnostic device and an otologic therapeutic device, each respectively comprising a nanoparticle conjugated with a material selected from the group consisting of lipids, proteins, growth factors, growth hormones, antioxidants, free radical scavengers, steroid preparations, and metabolically active substances. The conjugated material for the therapeutic device can also include chemotherapeutic drugs.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention.

What is claimed is:

1. A method for administering therapeutics to the inner ear comprising:

inserting a microcatheter transtympanically into the middle ear, wherein a terminal end of the microcatheter is at a position immediately adjacent to a membrane separating the middle ear from the inner ear;

injecting a nanoparticle into the microcatheter, wherein the position of the terminal end of the microcatheter permits diffusion of the nanoparticle through said membrane into the inner ear, wherein the nanoparticle comprises one or more therapeutic agents and an agent to facilitate diffusion through said membrane.

2. The method of claim 1 wherein said one or more therapeutic agent is selected from the group consisting of an antioxidant and a steroid.

3. The method of claim 2 wherein the antioxidant is N-acetylcysteine.

4. The method of claim 2 wherein the antioxidant is reduced glutathione.

5. The method of claim 2 wherein the steroid is dexamethasone.

6. The method of claim 1 wherein the membrane is the round window membrane.

7. The method of claim 1 wherein the membrane is the oval window.

8. The method of claim 1, wherein the agent to facilitate diffusion through said membrane is lipophilic polymer.

*9. A method for administering therapeutics to the inner ear comprising:*

*inserting a microcatheter transtympanically into the middle ear, wherein a terminal end of the microcatheter is at a position immediately adjacent to a membrane separating the middle ear from the inner ear;*

*injecting a nanoparticle into the microcatheter, wherein the position of the terminal end of the microcatheter permits diffusion of the nanoparticle through said membrane into the inner ear, wherein the nanoparticle comprises one or more therapeutic agents.*

*10. The method of claim 9, wherein the nanoparticle comprises a conjugated nanoparticle.*

*11. The method of claim 9, wherein the nanoparticle comprises a magnetic carrier configured to respond to an externally directed magnetic field.*

*12. The method of claim 9, wherein the nanoparticle comprises a water soluble polymer.*

*13. The method of claim 9, wherein the nanoparticle comprises an uncharged hydrophilic polymer.*

*14. The method of claim 9, wherein the nanoparticle comprises a micelle, and wherein the micelle comprises copolymers with hydrophilic shells and amino acids.*

*15. The method of claim 9, wherein the nanoparticle comprises a dendrimer.*

*16. The method of claim 9, wherein the nanoparticle comprises a substance perceptible to magnetic resonance imaging.*

*17. The method of claim 16, wherein the substance perceptible to magnetic resonance imaging comprises gadolinium.*

*18. The method of claim 9, wherein the one or more therapeutic agents comprises a growth factor or a growth hormone.*

*19. The method of claim 9, wherein the one or more therapeutic agents comprises a chemotherapeutic agent.*

*20. The method of claim 9, wherein the one or more therapeutic agents comprises an antibiotic.*

*21. The method of claim 9, wherein the one or more therapeutic agents comprises an antioxidant.*

*22. The method of claim 9, wherein the one or more therapeutic agents comprises a steroid.*

*23. The method of claim 9, wherein the membrane comprises at least one of a round window membrane or an oval window membrane.*

*24. The method of claim 9, wherein the membrane comprises a circulatory membrane.*

*25. The method of claim 9, wherein the injecting the nanoparticle comprises injecting a fluid comprising the nanoparticle.*

*26. A method for delivering one or more therapeutic agents to the inner ear comprising:*

*inserting a microcatheter transtympanically into the middle ear, wherein a terminal end of the microcatheter is at a position immediately adjacent to a membrane separating the middle ear from the inner ear;*

*using the microcatheter, delivering nanoparticles to the middle ear to permit their diffusion through the membrane into the inner ear, the nanoparticle comprising one or more therapeutic agents.*

*27. The method of claim 26 in which the nanoparticles are contained in a fluid.*

*28. The method of claim 26 in which the nanoparticles include a label.*

*29. The method of claim 26 in which the nanoparticles comprise an agent to facilitate diffusion through said membrane.*

*30. The method of claim 26 in which the nanoparticles comprise water-soluble polymers, lipophilic polymers, micelles, dendrimers, uncharged hydrophilic polymer, or magnetic targeted carriers.*

*31. The method of claim 26 in which the one or more therapeutic agents comprises one or more substances that promote hair cell regeneration.*

*32. The method of claim 26 in which the one or more therapeutic agents comprises one or more antioxidants or free radical scavengers.*

* * * * *